United States Patent [19]

Marantette et al.

[11] 4,229,139
[45] Oct. 21, 1980

[54] WATER POWERED HIGH SPEED MOTOR

[76] Inventors: William F. Marantette; Ruth B. Marantette, both of 20624 Earl St., Torrance, Calif. 90503

[21] Appl. No.: 35,723

[22] Filed: May 3, 1979

[51] Int. Cl.³ .............................................. F03B 13/04
[52] U.S. Cl. ...................................... 415/29; 415/118; 415/503; 433/132
[58] Field of Search ................... 415/29, 36, 118, 503; 433/120, 132; 308/76, 122; 408/240

[56] References Cited

U.S. PATENT DOCUMENTS

| 1,902,340 | 3/1933 | Schmidt | 415/29 |
| 3,298,103 | 1/1967 | Maurer | 433/132 |
| 3,465,442 | 9/1969 | Baldwin | 415/503 |
| 3,639,074 | 2/1972 | Killick | 415/503 |
| 3,767,320 | 10/1973 | Theis | 433/132 |
| 3,929,393 | 12/1975 | Marantette | 308/76 |
| 4,017,203 | 4/1977 | Marantette | 408/240 |

Primary Examiner—Billy J. Wilhite
Attorney, Agent, or Firm—Ralph B. Pastoriza

[57] ABSTRACT

The water powered motor includes a casing housing a rotor shaft. First and second water bearings of conical shape support opposite end portions of the shaft for high speed rotation. The central portion of the shaft has turbine wheels subject to high velocity water flow through the casing. The same high water pressure for driving the turbine also provides water to the water bearings to "float" the rotor shaft so that very high speeds can be attained with minimum friction. The preferred application for the motor is that of a high speed drill for drilling printed circuit boards. However, it may be miniaturized for use as a dentist's drill.

2 Claims, 4 Drawing Figures

WATER POWERED HIGH SPEED MOTOR

This invention relates generally to motors and more particularly to a high speed water turbine driven motor for drilling or grinding operations.

BACKGROUND OF THE INVENTION

Fluid driven drills such as by either air or water are known in the art. A preferred application for such types of drills is in dental work since there is no electricity involved at the portion of the instrument placed in a person's mouth. Moreover, very high speeds can be obtained utilizing air or water turbines to drive the drill.

Other applications for high speed drills is in the drilling of printed circuit boards. Thus rather than a hand held drill motor, these applications would normally involve a permanently mounted motor in a circuit drilling machine mechanism.

While the foregoing described motors have been satisfactory, their life is severely limited by the life of bearings utilized in rotatably mounting the rotor shaft carrying the drill or grinding tool or other instrument to be rotated. The enormously high speeds attainable by these drills simply cannot be handled by presently available mechanical type bearings. The only solution, accordingly, is to operate such drills at lower speeds or to redesign the bearings with expensive components far out of proportion of the overall cost of the tool and its particular job. Neither solution is really satisfactory.

BRIEF DESCRIPTION OF THE PRESENT INVENTION

With the foregoing considerations in mind, the present invention contemplates a high speed water driven motor for drills, grinders and the like in which high rotational speed can be maintained over extended periods of time without seriously affecting the bearings.

More particularlay, in accord with this invention, rather than mechanical type bearings, there are provided conically shaped water bearings so designed as to "float" the rotor shaft on a film of water derived from the high pressure water source utilized in driving appropriate turbine wheels on the rotor shaft. The continuous flow of water through the water bearings as well as through the turbine provides for a substantially frictionless bearing support over sustained high speed running periods, generated heat simply being carried away by the continuous flow of water through the bearing.

The foregoing described design lends itself well for drill motors in printed circuit drilling board systems as well as in hand held drills for use by dentists either for drilling purposes or grinding purposes.

BRIEF DESCRIPTION OF THE DRAWINGS

A better understanding of this invention will be had by now referring to the accompanying drawings, in which.

DETAILED DESCRIPTION OF THE INVENTION

Figure 1:
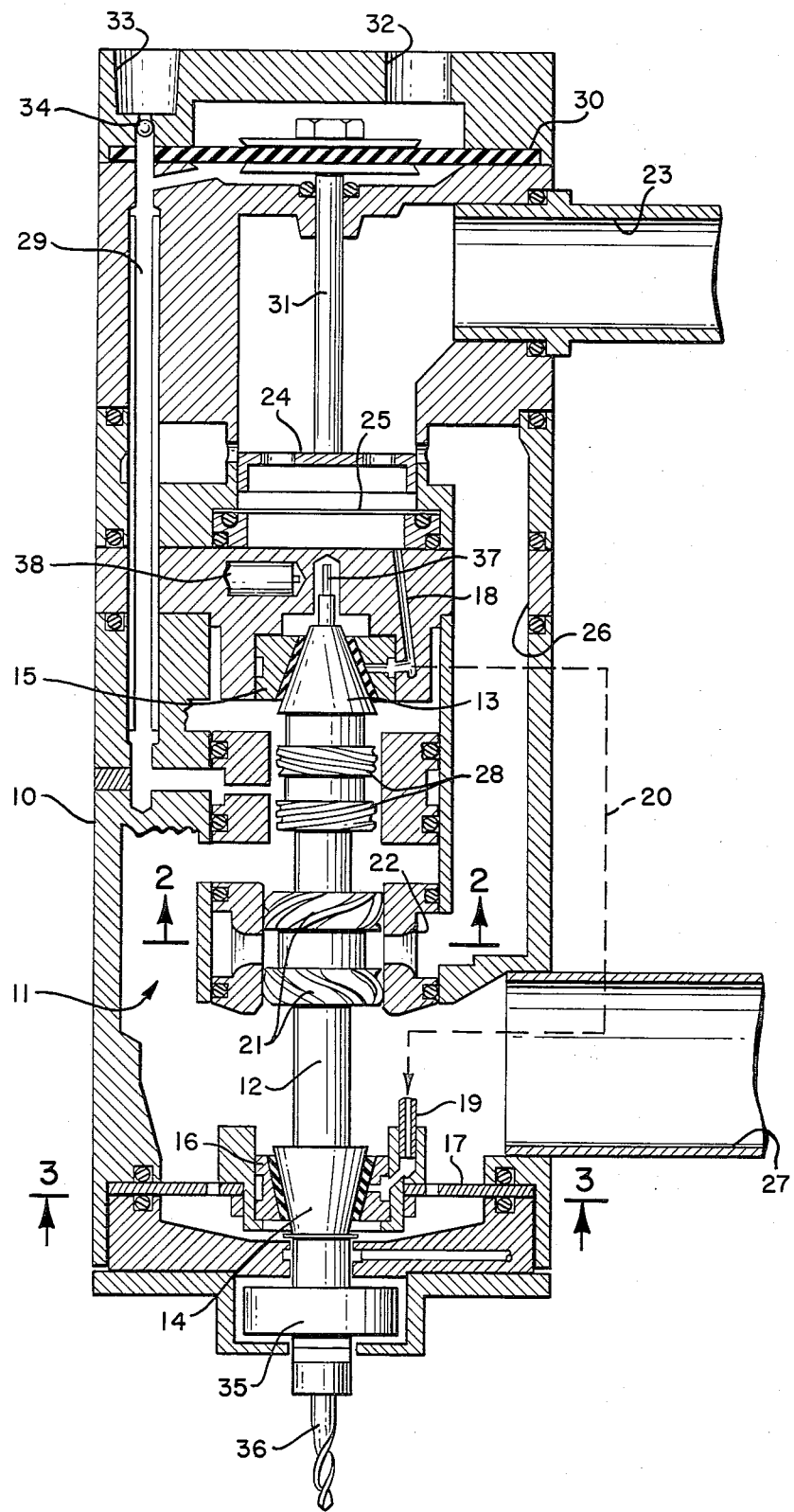
FIG. 1 is a cross sectional view with certain portions shown in full lines of the water powered high speed motor of this invention.

Referring first to FIG. 1, the water powered high speed motor comprises a casing 10 defining an inner chamber designated generally by the arrow 11.

Within the chamber 11 is a rotor shaft 12 having oppositely directed conical end surfaces 13 and 14. These end surfaces cooperate with first and second axially spaced oppositely directed conical bearing blocks 15 and 16 respectively. The first bearing block 15 is secured in a stationary position relative to the casing 10 while the second conical bearing block 16 is mounted to the casing for axial movement towards and away from the first bearing block. This mounting is accomplished by means of a resilient spring 17 which functions to bias the second block 16 in an axial direction to increase the engaging pressure between the bearing blocks and the conical end surfaces; that is, in an upward direction as viewed in FIG. 1.

The first and second bearing blocks 15 and 16 are provided with water inlet passages indicated at 18 and 19 respectively. The passage 19 is shown broken off to avoid obscuring portions of the drawings. However, this passage 19 connects to the passage 18 as indicated by the dashed line 20 in FIG. 1. The passages 18 and 19 pass into each bearing block to communicate with the surfaces of the bearing blocks and the conical end surfaces of the shaft.

Shown on the shaft 12 between the first and second bearing blocks 15 and 16 are turbine wheel means 21 in the form of first and second axially spaced wheels with turbine blades forming mirror images of each other such that water directed tangentially to the blades will cause rotation of the shaft 12. Towards this latter end, there is provided a turbine wheel water inlet nozzle 22 which guides water through the turbine wheels 21 and thence from the turbine wheels into the inner chamber 11 of the casing 10.

Referring to the upper portion of FIG. 1, there is shown at 23 a high water pressure inlet passage for directing water through the casing to the water bearings and turbine wheels. More particularly, water from the inlet passage 23 passes through a valve head 24 and water filter screen 25 to the bearing passage 18 and the connected bearing passage 19 for the bearings 15 and 16 respectively. The high pressure water received in these inlet passages essentially results in the conical end surfaces of the shaft being caused to float on a thin film of water covering the engaging surfaces of the bearing blocks to provide a water bearing. Because of the biasing of the second block 16 relative to the first block 15 as by the spring 17, the blocks can seperate axially slightly to accomodate the thin film of water between the bearing surfaces and the conical shaft end surfaces. It will be understood that water will continuously flow through the inlet passages to the bearings and thence from between the bearing surfaces into the inner chamber 11 of the casing 10.

Referring again to the upper portion of FIG. 1, the same high pressure water in the inlet passage 23 also is directed through a latteral valve port cooperating with the valve head 24 and partially eclipsed by this valve head. This lateral port leads into a passage 26 for directing the water through the inlet nozzle structure 22 between the turbine wheels 21. Water will rotate the turbine wheels 21 passing through these wheels into the inner chamber 11 of the casing 10.

The water from the bearings as well as coming from the turbine wheels into the chamber 11 will then be exhausted through an appropriate outlet passage 27 shown in the lower portion of the casing 10 in FIG. 1.

It can be appreciated from the foregoing that the same high pressure water in the inlet passage 23 serves to control not only the water bearing operation but also to rotate the rotor shaft, the water bearing being such as to permit very high speed rotation of the rotor shaft by the flow of water through the turbine wheels without any significant wear on the bearing surfaces. In this latter respect, it will be understood that any heat developed is continuously being carried away by the water film itself constituting the actual bearing and holding the bearing surfaces in a seperated relationship.

In the particular embodiment of FIG. 1, there is additionally provided a rotor shaft speed control means to, in effect, govern the speed of rotation of the rotor shaft. With particular reference to the central portion of FIG. 1, this speed control means includes tachometer pump means in the form of pump wheels 28 secured to the shaft 12 between the turbine wheels 21 and first bearing block 15. The wheels 28 have slanted blades in mirror image relationship such that rotation of the shaft results in a build up in water pressure between the wheels. This build up in water pressure is communicated through a water passage 29 extending up the left of the casing 10 to be applied under a rubber diaphram 30 supporting the valve head 24 by way of valve stem 31.

The area above the rubber diaphram 30 is subject to controlled air pressure by an input duct 32.

When the foregoing components, the tachometer wheels rotate with the rotor shaft and will generate a water pressure constituting a function of the speed of this shaft, this water pressure being applied under the rubber diaphram 30 to oppose a given constant air pressure applied through the inlet port 32 above the diaphram. As described heretofore, the flow of high pressure inlet water in the passage 23 to the turbine wheels 21 takes place through lateral valve ports partially eclipsed by the valve head 24, these valve ports connecting the inlet water passage 23 with the passage 26 leading to the turbine wheels. Accordingly, when the valve head 24 moves downwardly as a result of downward movement of the rubber diaphram 30 and valve stem 31, the lateral ports are opened up further to thereby permit an increased flow of water to take place from the passage 23 to the passage 26 and thus to the turbine wheels. When the valve head 24 is moved upwardly, on the other hand, the lateral ports are closed off more thereby decreasing the water flow from the inlet passage 23 to the passage 26 and to the turbine wheels.

From the foregoing, it can thus be seen that when the generated water pressure by the tachometer wheels 28 exceeds a predetermined pressure, such predetermined pressure being applied to the top of the rubber diaphram 30 through the inlet port 32, the raising up of the diaphram 30 and thus the valve head 24 will close off the lateral ports more than they are already eclipsed to thereby reduce the water flow to the turbine wheels. This action results in a slowing down of the speed of the rotor shaft and thus a decrease in the generated water pressure by the tachometer wheels 28 and thus a decrease in the water pressure beneath the diaphram 30. It will thus be seen that a self regulation takes place so that the speed of the rotor is held at a substantially constant value.

If it is desired to run the rotor 12 at maximum speed, a very high pressure may be applied to the top of the rubber diaphram 30 through the inlet port 32 to seat completely this diaphram on the periphery of the opening through which the stem 31 extends thus sealing this opening and further positioning the valve head 24 well below the lateral ports so that maximum flow can take place from the passage 23 to the passage 26 and thus maximum flow through the turbine wheels will take place.

In running the rotor at maximum speed, it is desirable not to have high pressure generated by the tachometer wheels 28 as described under normal governing conditions. Accordingly, there is provided an air inlet 33 at the top of the casing through which air can be forced through a check valve 34 into the fluid passage 29 to force all liquid out from between the tachometer wheels 28 thereby reducing any friction which would otherwise be caused by the presence of liquid between these wheels. When these conditions are met, the rotor 12 could run at maximum speed.

The water bearings comprising the tapered end surfaces 13 and 14 on the rotor shaft 12 and the first and second bearing blocks 15 and 16 maybe designed in accord with the teachings of our U.S. Pat. No. 3,929,393 issued Dec. 30, 1975 which discloses a water-rubber bearing system.

Where the motor described in FIG. 1 is to be used in a circuit board drilling system, an appropriate centrifugal type clutch 35 could be secured to the rotor shaft 12, this clutch 35 operating in accord with the teachings of our U.S. Pat. No. 4,017,203 issued Apr. 12, 1977. An appropriate drill 36 is shown secured in the centrifugal clutch 35.

If it is desired to monitor the speed of the drill 36, the motor may incorporate an appropriate means for detecting the rate of rotation of the rotor shaft 12. In FIG. 1, one such means is shown in the form of a magnetic stainless steel flat structure secured to the upper end of the rotor 12 above the conical end surface 13 as shown at 37. Embedded adjacent to this stainless steel flat 37 is a magnetic pickup 38 responsive to the change in flux resulting from rotation of the flat 37.

The variable signal from the magnetic pickup 38 can readily be converted to an output rpm reading thus providing a continuous monitoring of the rotor speed.

Figure 2:
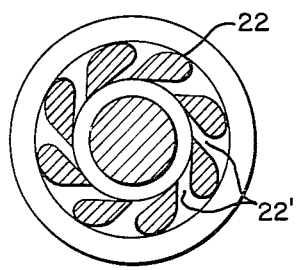
FIG. 2 is a cross section of an inlet nozzle for a turbine portion of the motor looking in the direction of the arrows 2—2 of FIG. 1.

Referring now to FIG. 2, there is shown in the cross sectional view further details of the turbine wheel water inlet nozzle 22. As shown, there are provided tangential passages 22' defined circumferentially about the inlet of the turbine wheels.

Figure 3:
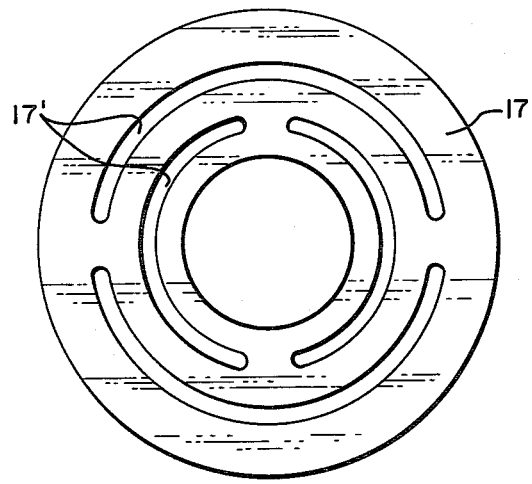
FIG. 3 is a plan view of a disk type spring looking in the direction of the arrows 3—3 of FIG. 1 and, FIG. 4 is a cross section with certain components shown in full lines of a modified embodiment of the motor of this invention designed for hand held operation.

FIG. 3 illustrates the spring 17 in further detail wherein the arcuate slots 17' will provide the desired resiliency for the second bearing 16 of FIG. 1 in an axial direction but inhibit any movement in a radial or lateral direction.

Figure 4:
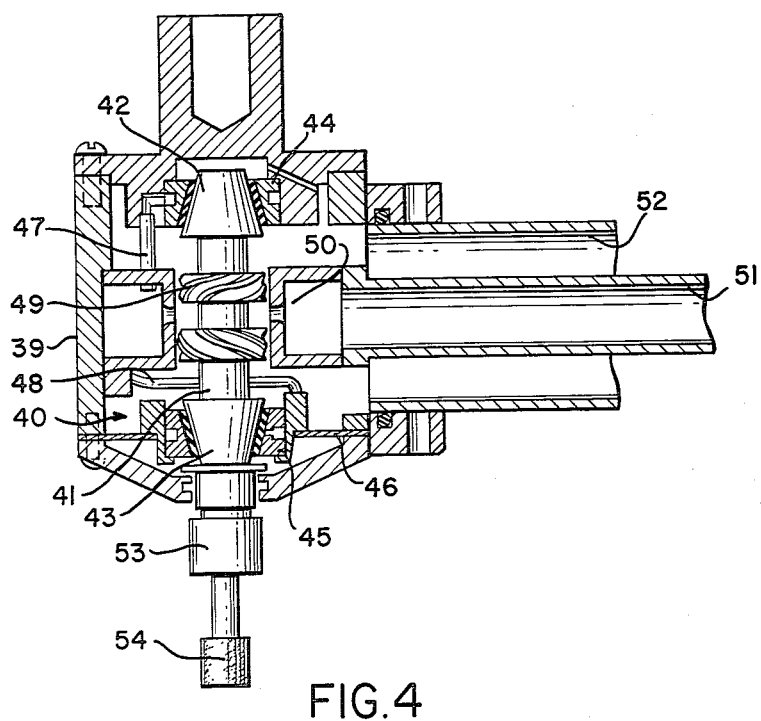

Referring now to FIG. 4, there is shown a modified embodiment of the water motor of this invention in the form of a hand held type motor and wherein the speed control means is not included. However, the remaining basic components are essentially the same as those described in conjunction with FIG. 1.

Thus, with specific reference to FIG. 4 the motor includes a casing 39 defining an inner chamber 40. A rotor shaft 41 in turn is provided with oppositely directed conical end surfaces 42 and 43 cooperating with first and second bearing blocks 44 and 45. The second bearing block 45 is again supported by a spring structure 46 for limited axial movement and to bias the same towards the bearing block 44. The rotor 41 is thus held captive between the bearing blocks.

Suitable inlet water passages 47 and 48 are provided for the water blocks so that under high pressure water, there results a water bearing or thin film of water between the tapered surfaces of the shaft and blocks respectively all as described with respect with FIG. 1.

Also as in the case of FIG. 1, the rotor shaft 41 includes turbine wheel means 49 having a nozzle input structure 50 for receiving water under high pressure in an inlet water passage 51. This high pressure water passes not only through the turbine blades 49 but also into the passages 47 and 48 for the water bearings as in the case of FIG. 1. From the water bearings and from the top and under side of the respective turbine wheels the water passes to the inner chamber 40 and thence through an outlet passage which is coaxially arranged about the inlet passage 51. This coaxial outlet passage is indicated at 52.

In the embodiment of FIG. 4, rather than a centrifugal clutch, there is shown a simple collet 53 for supporting an instrument such as a grinding wheel 54 to be rotated at high speed.

By avoiding the use of the speed control in the embodiment of FIG. 4, the overall size of the motor can be greatly reduced. Actually, the straight-line torque characteristic of the turbine coupled with the fast-rising friction characteristic of the water bearings combine to maintain speed as load is applied even without the speed controller described in conjunction with FIG. 1.

From all the foregoing, it will thus be evident that the present invention has provided a greatly improved water powered high speed motor. The use of water bearings in combination with a turbine wherein the same high water pressure source operates the bearings as well as rotates the turbine wheels enables very high rotor speeds to be acheived without requiring frequent replacement of bearings nor oversized complicated and expensive bearing structures.

We claim:
1. A water powered high speed motor, including, in combination;
 (a) a casing defining an inner chamber;
 (b) a rotor shaft in said chamber having oppositely directed conical end surfaces;
 (c) first and second axially aligned oppositely directed conical bearing blocks engaging in mating relationship said end surfaces to mount said rotor shaft in said casing, said first bearing block being fixed to said casing and said second bearing block being resiliently mounted to said casing for axial movement towards and away from said first bearing block;
 (d) means biasing said second bearing block in an axial direction to increase the engaging pressure between said bearing blocks and conical end surfaces;
 (e) water inlet means passing into each bearing block to communicate with the surfaces of the bearing blocks and conical surfaces of the shaft;
 (f) turbine wheel means on said shaft between said first and second bearing blocks;
 (g) turbine wheel water inlet nozzle means communicating with said turbine wheel means;
 (h) a high water pressure inlet passage in said casing for directing water under high pressure into said water inlet means in each bearing block so that the conical end surfaces of said shaft float on a film of water covering the engaging surfaces of said bearing blocks to provide a water bearing, said high water pressure inlet passage also connecting to said turbine wheel water inlet nozzle to pass water under high pressure through said turbine wheel means to rotate said shaft, water from between the engaging surfaces of said bearing blocks and conical end portions and from the turbine wheel means passing into said chamber; and
 (i) a water outlet passage from said chamber to the exterior of said casing to exhaust water from said chamber, whereby high pressure water simultaneously serves to float said rotor shaft in its bearings and rotate said shaft at high speed.

2. A motor according to claim 1, having rotor shaft speed control means including tachometer pump means connected to said rotor shaft for generating a water pressure constituting a direct function of the speed of said shaft; and valve means in said casing for controlling water flow from said water inlet passage to said turbine wheel water inlet nozzle, said valve means being responsive to said water pressure generated by said tachometer pump to decrease the water flow to said inlet nozzle when said generated pressure exceeds a first given value and increase the water flow to said inlet nozzle when said predetermined pressure drops below a second given value whereby the rotor shaft speed can be maintained substantially constant even though the pressure of the inlet water may vary.

* * * * *